(12) United States Patent
Kato

(10) Patent No.: US 7,666,140 B2
(45) Date of Patent: Feb. 23, 2010

(54) ULTRASONIC IMAGING METHOD AND ULTRASONIC DIAGNOSTIC APPARATUS

(75) Inventor: Sei Kato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 759 days.

(21) Appl. No.: 10/809,117

(22) Filed: Mar. 25, 2004

(65) Prior Publication Data

US 2004/0193053 A1    Sep. 30, 2004

(30) Foreign Application Priority Data

Mar. 27, 2003    (JP)    ............... 2003-086729

(51) Int. Cl.
*A61B 8/00* (2006.01)

(52) U.S. Cl. .................................... 600/443

(58) Field of Classification Search ............... 600/437, 600/443; 382/128
See application file for complete search history.

(56) References Cited

U.S. PATENT DOCUMENTS

| | | | |
|---|---|---|---|
| 5,559,901 A * | 9/1996 | Lobregt ............. | 382/256 |
| 5,938,607 A | 8/1999 | Jago et al. | |
| 6,500,123 B1 * | 12/2002 | Holloway et al. ........... | 600/443 |
| 6,638,225 B2 | 10/2003 | Kamiyama | |
| 6,793,626 B2 * | 9/2004 | Tsuzuki .................. | 600/458 |
| 6,878,114 B2 * | 4/2005 | Murashita ............... | 600/443 |
| 6,984,211 B2 * | 1/2006 | Hao et al. ................ | 600/443 |
| 2002/0120195 A1 * | 8/2002 | Hossack et al. ........... | 600/443 |
| 2004/0158155 A1 * | 8/2004 | Njemanze ................ | 600/454 |
| 2005/0004469 A1 * | 1/2005 | Tsuzuki .................. | 600/458 |
| 2005/0119568 A1 * | 6/2005 | Salcudean et al. .......... | 600/437 |
| 2006/0052396 A1 * | 3/2006 | Berg et al. ............ | 514/255.06 |
| 2006/0173320 A1 * | 8/2006 | Radulescu ............... | 600/438 |
| 2007/0049824 A1 * | 3/2007 | Konofagou et al. ........ | 600/437 |

FOREIGN PATENT DOCUMENTS

| | | |
|---|---|---|
| JP | 10-179586 | 7/1998 |
| JP | 2000-139920 | 5/2000 |
| JP | 2000-152928 | 6/2000 |
| JP | 2000-300557 | 10/2000 |

* cited by examiner

*Primary Examiner*—Eric F Winakur
*Assistant Examiner*—Michael T Rozanski
(74) *Attorney, Agent, or Firm*—Armstrong Teasdale LLP

(57) ABSTRACT

For the purpose of suitably making comparison between a previously acquired reference image and a real-time image currently being acquired, a reference image and a scan condition therefor are stored, the reference image and scan condition are read out, a real-time image is acquired after setting the scan condition, and the reference image and real-time image are displayed side by side.

10 Claims, 8 Drawing Sheets

ULTRASONIC IMAGING METHOD AND ULTRASONIC DIAGNOSTIC APPARATUS

CROSS REFERENCE TO RELATED APPLICATIONS

This application claims the benefit of Japanese Application No. 2003-086729 filed Mar. 27, 2003.

BACKGROUND OF THE INVENTION

The present invention relates to an ultrasonic imaging method and ultrasonic diagnostic apparatus, and more particularly to an ultrasonic imaging method and ultrasonic diagnostic apparatus by which comparison between a previously acquired reference image and a real-time image currently being acquired can be suitably made.

Conventionally, there has been known an ultrasonic diagnostic apparatus that stores a reference image, reads out the reference image, and displays the reference image with a real-time image superimposed or arranged side by side. (For example, see Patent Document 1).

[Patent Document 1]
Japanese Patent Application Laid Open No. 2000-300557 (claim 1).

In the conventional ultrasonic diagnostic apparatus, however, no consideration is given to possible difference between the scan conditions for the reference image and for the real-time image.

If a difference exists between the scan conditions, a problem arises in that a region unchanged from the past to the present looks as if it were changed or a region changed from the past to the present looks as if it were unchanged.

SUMMARY OF THE INVENTION

It is therefore an object of the present invention to provide an ultrasonic imaging method and ultrasonic diagnostic apparatus by which comparison between a previously acquired reference image and a real-time image currently being acquired can be suitably made by making their scan conditions the same.

In a first aspect, the present invention provides an ultrasonic imaging method characterized in comprising: storing a reference image and a scan condition therefor; reading said reference image and said scan condition; setting said scan condition and acquiring a real-time image; and displaying said reference image and said real-time image side by side.

According to the ultrasonic imaging method of the first aspect, a scan condition for a reference image is stored, the scan condition is read out to acquire a real-time image, and the reference image and real-time image are displayed side by side. Thus, images acquired with the same scan condition can be compared; for example, a reference image acquired before medical treatment and a real-time image after medical treatment can be compared to accurately estimate the effect of the medical treatment.

In a second aspect, the present invention provides the ultrasonic imaging method having the aforementioned configuration, characterized in comprising: calculating a correlation coefficient between said reference image and said real-time image throughout or partially; and displaying the calculated correlation coefficient.

According to the ultrasonic imaging method of the second aspect, a correlation coefficient between corresponding regions in the reference image and real-time image is calculated and displayed. Thus, the degree of difference between the reference image and real-time image can be objectively evaluated.

In a third aspect, the present invention provides an ultrasonic imaging method characterized in comprising: storing a reference image and a scan condition therefor; reading said reference image and said scan condition; setting said scan condition and acquiring a plurality of real-time images at different scan plane angles; calculating a correlation coefficient between said reference image and each of said real-time images throughout or partially; and displaying said reference image and said real-time image having the highest correlation coefficient side by side.

According to the ultrasonic imaging method of the third aspect, a plurality of real-time images are acquired at different scan plane angles, and the real-time image having the highest correlation coefficient with respect to the reference image is selected and displayed. As this makes it permissible to put the ultrasonic probe against a subject somewhat imprecisely, it reduces the work load on a human operator.

In a fourth aspect, the present invention provides the ultrasonic imaging method having the aforementioned configuration, characterized in comprising: displaying said highest correlation coefficient.

According to the ultrasonic imaging method of the fourth aspect, a correlation coefficient between corresponding regions of the reference image and real-time image being displayed is presented. Thus, the degree of difference between the reference image and real-time image being displayed can be objectively evaluated.

In a fifth aspect, the present invention provides the ultrasonic imaging method having the aforementioned configuration, characterized in comprising: displaying in a hold manner the maximum value of the correlation coefficient from the beginning of acquisition of the real-time image up to the present.

According to the ultrasonic imaging method of the fifth aspect, since the maximum value of the correlation coefficient up to the present is displayed in a hold manner, the way in which the ultrasonic probe is put against the subject can be adjusted to maximize the correlation coefficient and thereby maintain the best way.

In a sixth aspect, the present invention provides the ultrasonic imaging method having the aforementioned configuration, characterized in comprising: calculating a correlation coefficient for a region outside of a region of interest defined in said reference image or in said real-time image.

According to the ultrasonic imaging method of the sixth aspect, if a region to be treated is defined as a region of interest, for example, a portion which changes between before and after medical treatment is excluded in the calculation of a correlation coefficient, and therefore, the correlation coefficient between the reference image and real-time image can be accurately calculated.

In a seventh aspect, the present invention provides the ultrasonic imaging method having the aforementioned configuration, characterized in comprising: calculating a correlation coefficient for a correlation comparison region defined in said reference image or in said real-time image.

According to the ultrasonic imaging method of the seventh aspect, if a region other than a region to be treated is defined as a correlation comparison region, for example, a portion which changes between before and after medical treatment is excluded in the calculation of a correlation coefficient, and therefore, the correlation coefficient between the reference image and real-time image can be accurately calculated.

In an eighth aspect, the present invention provides the ultrasonic imaging method having the aforementioned configuration, characterized in comprising: displaying said reference image and said real-time image superimposed in response to a command by an operator.

According to the ultrasonic imaging method of the eighth aspect, the reference image and real-time image can be displayed superimposed to facilitate estimation of the presence or degree of change.

In a ninth aspect, the present invention provides the ultrasonic imaging method having the aforementioned configuration, characterized in comprising: storing a measurement result for a target region in said reference image; and reading said measurement result and displaying it when displaying said reference image.

According to the ultrasonic imaging method of the ninth aspect, since one can know a pre-treatment value of, for example, the diameter or area of a region to be treated, the effect of treatment can be numerically estimated.

In a tenth aspect, the present invention provides the ultrasonic imaging method having the aforementioned configuration, characterized in comprising: storing said reference image and said scan condition in a server on a network.

According to the ultrasonic imaging method of the tenth aspect, if one who has stored a reference image and a scan condition therefor in a server makes the server public, others can read and use the reference image and scan condition.

In an eleventh aspect, the present invention provides an ultrasonic diagnostic apparatus characterized in comprising: an ultrasonic probe; transmitting/receiving means for driving said ultrasonic probe to transmit ultrasonic pulses into a subject and receive ultrasonic echoes from inside the subject and outputting received data; ultrasonic image producing means for producing an ultrasonic image from the resulting received data; reference image storage means for storing a reference image; scan condition storage means for storing a scan condition for the reference image; automatic scan condition setting means for reading said scan condition and setting it; ultrasonic image display means for reading said reference image and displaying said reference image and a real-time image side by side.

According to the ultrasonic diagnostic apparatus of the eleventh aspect, the ultrasonic imaging method of the first aspect can be suitably implemented.

In a twelfth aspect, the present invention provides the ultrasonic diagnostic apparatus having the aforementioned configuration, characterized in comprising: correlation coefficient calculating means for calculating a correlation coefficient between said reference image and said real-time image throughout or partially; and correlation coefficient display means for displaying the calculated correlation coefficient.

According to the ultrasonic diagnostic apparatus of the twelfth aspect, the ultrasonic imaging method of the second aspect can be suitably implemented.

In a thirteenth aspect, the present invention provides an ultrasonic diagnostic apparatus characterized in comprising: an ultrasonic probe; transmitting/receiving means for driving said ultrasonic probe to transmit ultrasonic pulses into a subject and receive ultrasonic echoes from inside the subject and outputting received data; ultrasonic image producing means for producing an ultrasonic image from the resulting received data; reference image storage means for storing a reference image; scan condition storage means for storing a scan condition for the reference image; automatic scan condition setting means for reading said scan condition and setting it; scan plane angular scanning means for acquiring a plurality of real-time images at different scan plane angles; correlation coefficient calculating means for calculating a correlation coefficient between said reference image and each of said real-time images throughout or partially; and ultrasonic image display means for displaying said reference image and said real-time image having the highest correlation coefficient side by side.

According to the ultrasonic diagnostic apparatus of the thirteenth aspect, the ultrasonic imaging method of the third aspect can be suitably implemented.

In a fourteenth aspect, the present invention provides the ultrasonic diagnostic apparatus having the aforementioned configuration, characterized in comprising: correlation coefficient display means for displaying said highest correlation coefficient.

According to the ultrasonic diagnostic apparatus of the fourteenth aspect, the ultrasonic imaging method of the fourth aspect can be suitably implemented.

In a fifteenth aspect, the present invention provides the ultrasonic diagnostic apparatus having the aforementioned configuration, characterized in comprising: correlation coefficient maximum value display means for displaying in a hold manner the maximum value of the correlation coefficient from the beginning of acquisition of the real-time image up to the present.

According to the ultrasonic diagnostic apparatus of the fifteenth aspect, the ultrasonic imaging method of the fifth aspect can be suitably implemented.

In a sixteenth aspect, the present invention provides the ultrasonic diagnostic apparatus having the aforementioned configuration, characterized in that: said correlation coefficient calculating means calculates a correlation coefficient for a region outside of a region of interest defined in said reference image or in said real-time image.

According to the ultrasonic diagnostic apparatus of the sixteenth aspect, the ultrasonic imaging method of the sixth aspect can be suitably implemented.

In a seventeenth aspect, the present invention provides the ultrasonic diagnostic apparatus having the aforementioned configuration, characterized in that: said correlation coefficient calculating means calculates a correlation coefficient for a correlation comparison region defined in said reference image or in said real-time image.

According to the ultrasonic diagnostic apparatus of the seventeenth aspect, the ultrasonic imaging method of the seventh aspect can be suitably implemented.

In an eighteenth aspect, the present invention provides the ultrasonic diagnostic apparatus having the aforementioned configuration, characterized in comprising: combined-display means for displaying said reference image and said real-time image superimposed in response to a command by an operator.

According to the ultrasonic diagnostic apparatus of the eighteenth aspect, the ultrasonic imaging method of the eighth aspect can be suitably implemented.

In a nineteenth aspect, the present invention provides the ultrasonic diagnostic apparatus having the aforementioned configuration, characterized in comprising: measurement result storage means for storing a measurement result for a target region in said reference image; and measurement result display means for reading said measurement result and displaying it when displaying said reference image.

According to the ultrasonic diagnostic apparatus of the nineteenth aspect, the ultrasonic imaging method of the ninth aspect can be suitably implemented.

In a twentieth aspect, the present invention provides the ultrasonic diagnostic apparatus having the aforementioned configuration, characterized in that: said reference image storage means and said scan condition storage means reside in said ultrasonic diagnostic apparatus itself, and in addition, in a server on a network.

According to the ultrasonic diagnostic apparatus of the twentieth aspect, the ultrasonic imaging method of the tenth aspect can be suitably implemented. Moreover, the storage capacity of the ultrasonic diagnostic apparatus itself need not to be increased, thus simplifying the configuration.

In a twenty-first aspect, the present invention provides the ultrasonic diagnostic apparatus having the aforementioned configuration, characterized in that: said reference image storage means and said scan condition storage means reside not in said ultrasonic diagnostic apparatus itself but in a server on a network.

According to the ultrasonic diagnostic apparatus of the twenty-first aspect, the ultrasonic imaging method of the tenth aspect can be suitably implemented. Moreover, the storage capacity of the ultrasonic diagnostic apparatus itself may be small, thus simplifying the configuration.

According to the ultrasonic imaging method and ultrasonic diagnostic apparatus of the present invention, comparison between a previously acquired reference image and a real-time image currently being acquired can be suitably made by making their scan conditions the same.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings.

First Embodiment

Figure 1:
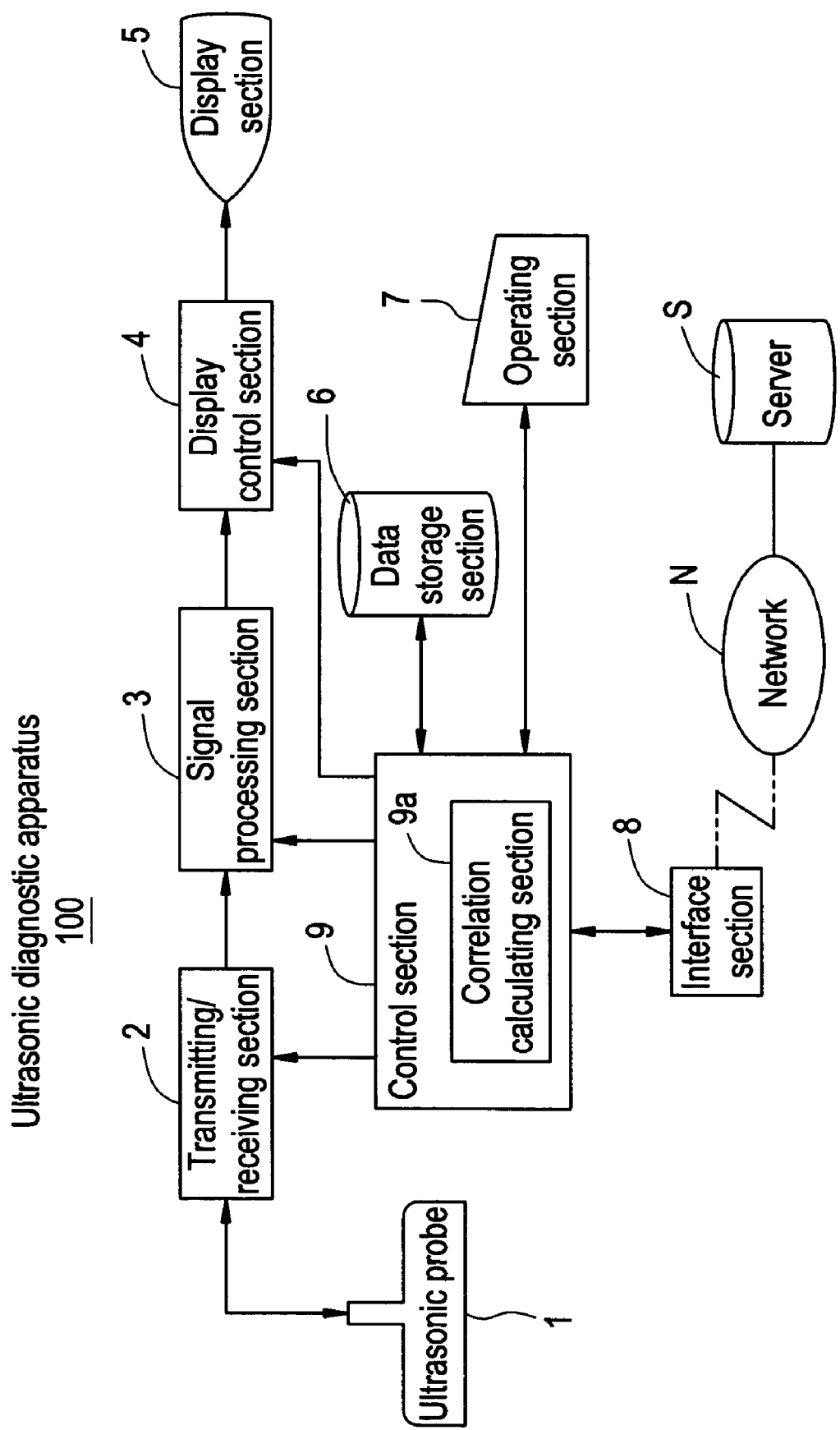
FIG. 1 is a block diagram showing an ultrasonic diagnostic apparatus in accordance with a first embodiment.

FIG. 1 is a block diagram of an ultrasonic diagnostic apparatus 100 in accordance with a first embodiment.

The ultrasonic diagnostic apparatus 100 comprises an ultrasonic probe 1, a transmitting/receiving section 2 for driving the ultrasonic probe 1 to conduct a scan in a scan plane and output an acoustic line signal, a signal processing section 3 for generating an ultrasonic image signal based on the acoustic line signal, a display control section 9 for generating image data from the ultrasonic image signal, a display section 5 for displaying an ultrasonic image based on the image data, a data storage section 6 for storing the generated image data and the like, an operating section 7 provided with a keyboard and pointing device for an operator to input commands, an interface section 8 for connection with a server S via an external network N, and a control section 9 including a correlation calculating section 9a for calculating a correlation coefficient between two ultrasonic images, and controlling the overall operation.

Figure 2:
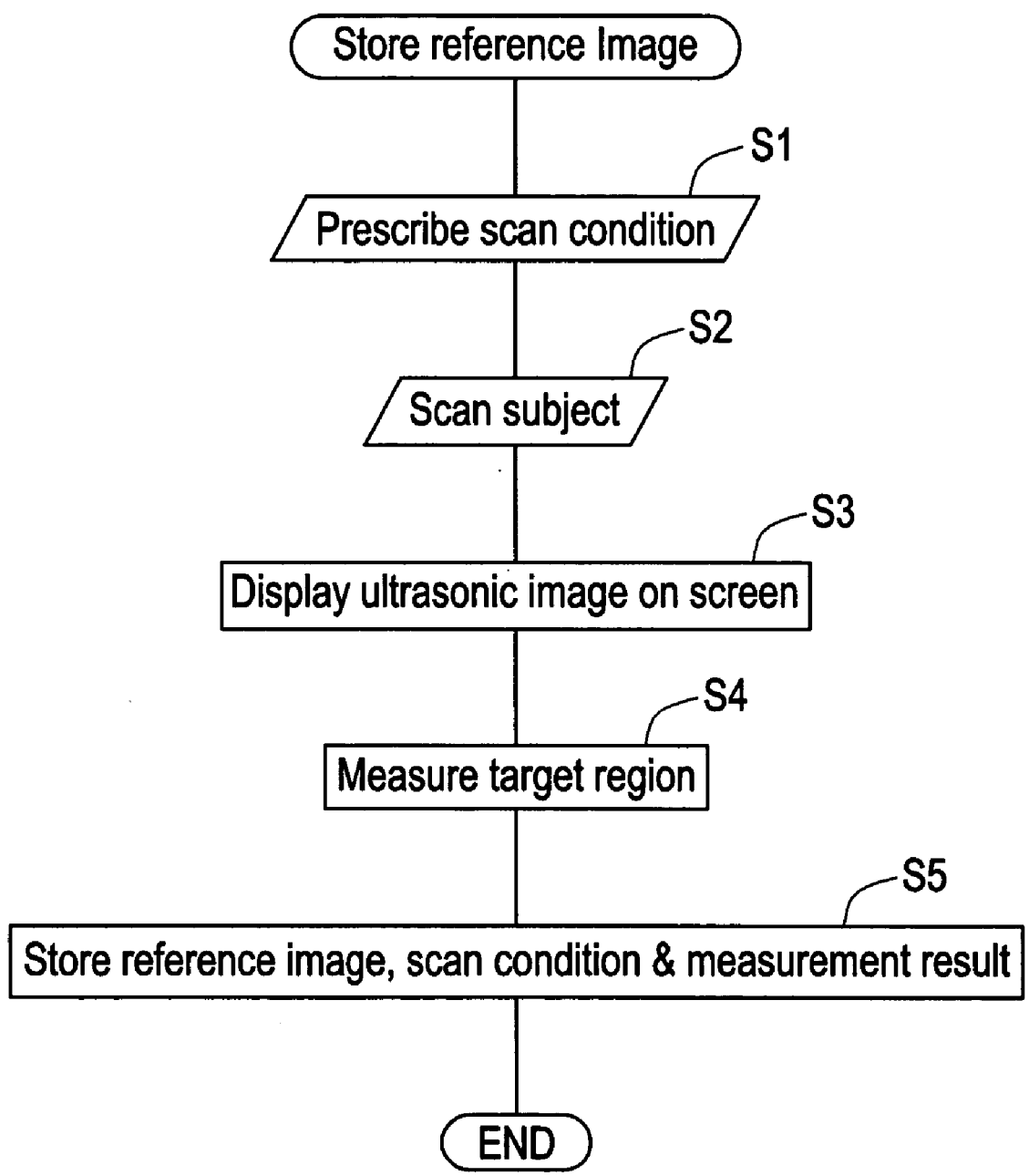
FIG. 2 is a flow chart showing operations and processes in storing a reference image by the ultrasonic diagnostic apparatus in accordance with the first embodiment.

FIG. 2 is a flow chart showing operations and processes in storing a reference image using the ultrasonic diagnostic apparatus 100.

At Step S1, an operator operates the operating section 7 and prescribes a scan condition.

At Step S2, the operator puts the ultrasonic probe 1 against a subject so that a region to be treated is contained in a scan plane, and performs a scan.

At Step S3, the ultrasonic diagnostic apparatus 100 produces an ultrasonic image, and displays it at the display section 5.

At Step S4, after an ultrasonic image serving as a reference image has been obtained, the operator uses a measurement function of the ultrasonic diagnostic apparatus 100 to measure the size or area of the region to be treated in the reference image.

At Step S5, the ultrasonic diagnostic apparatus 100 stores the reference image, scan condition and measurement result therefor in both or one of the data storage section 6 and server S on the network N in response to a command by the operator.

Figure 3:
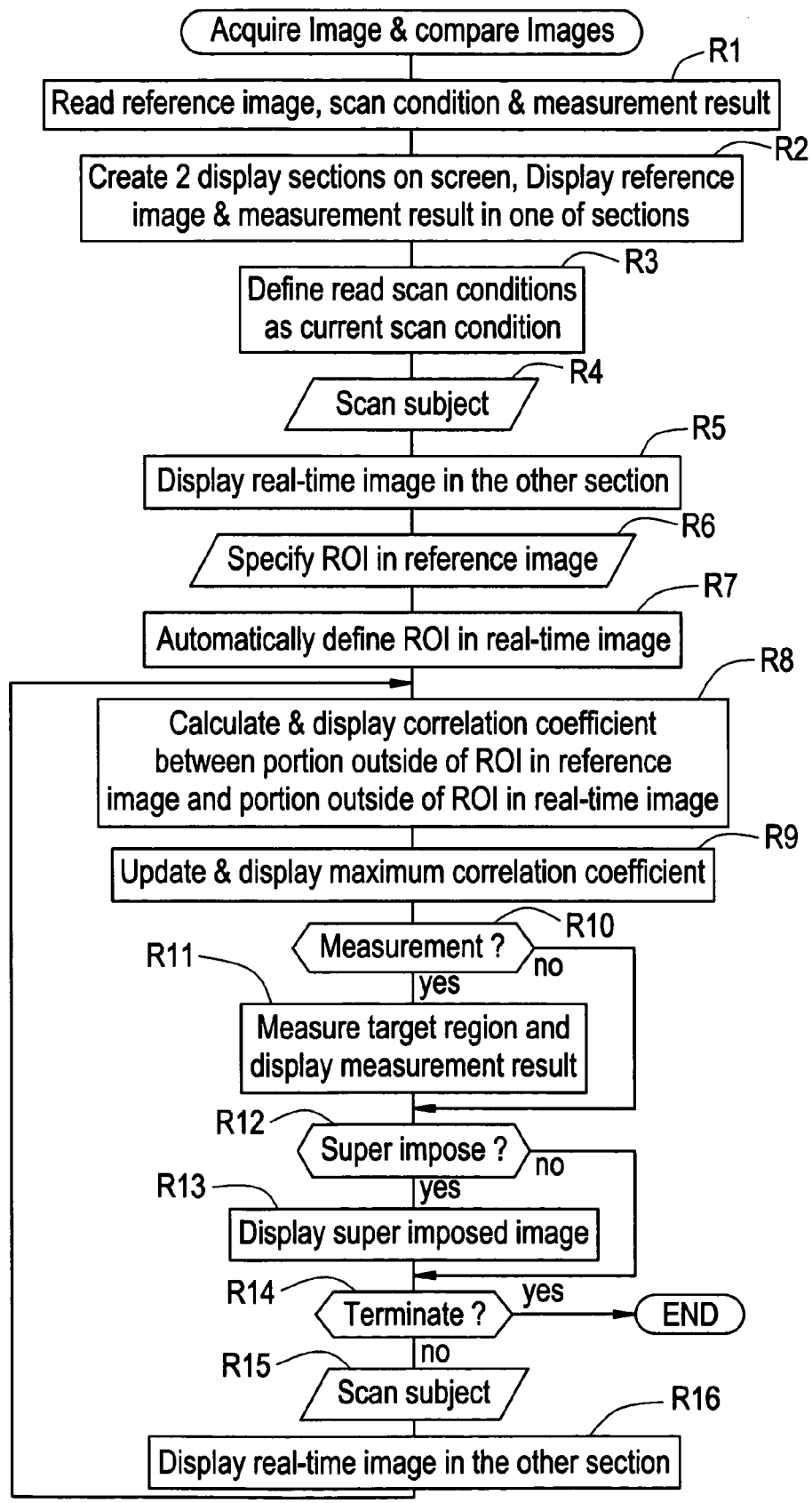
FIG. 3 is a flow chart showing operations and processes in acquiring a real-time image and comparing it with a reference image by the ultrasonic diagnostic apparatus in accordance with the first embodiment.

FIG. 3 is a flow chart showing operations and processes in acquiring a real-time image and comparing it with the reference image using the ultrasonic diagnostic apparatus 100.

At Step R1, the ultrasonic diagnostic apparatus 100 reads the reference image, scan condition and measurement result therefor from the data storage section 6 or server S in response to a command by the operator. The reading may be made on a reference image and a scan condition therefor stored on the server S and made public by a third party.

Figure 4:
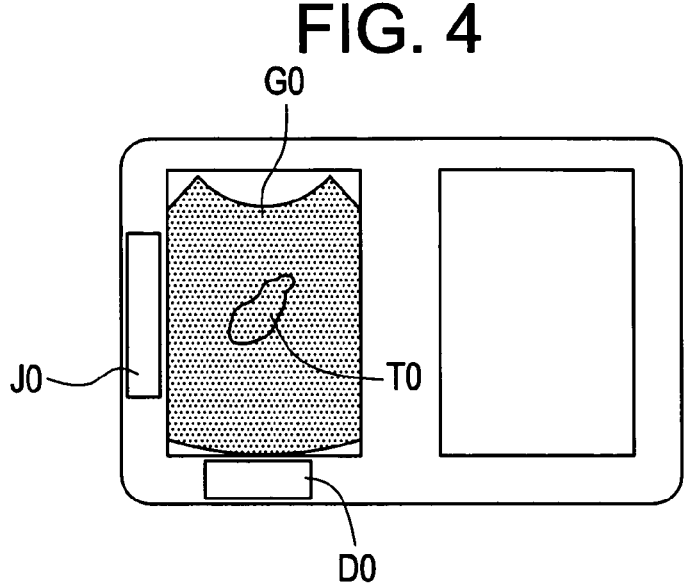
FIG. 4 is an explanatory diagram showing a screen on which a reference image is displayed.

At Step R2, the ultrasonic diagnostic apparatus 100 creates two display sections on a screen, as shown in FIG. 4, and displays a reference image G0, a scan condition J0, and a measurement result D0 in one of the sections. T0 designates a region to be treated before medical treatment.

At Step R3, the ultrasonic diagnostic apparatus 100 sets the read scan condition as the current scan condition.

At Step R4, the operator puts the ultrasonic probe 1 against the subject so that the region to be treated is contained in a scan plane, and performs a scan.

Figure 5:
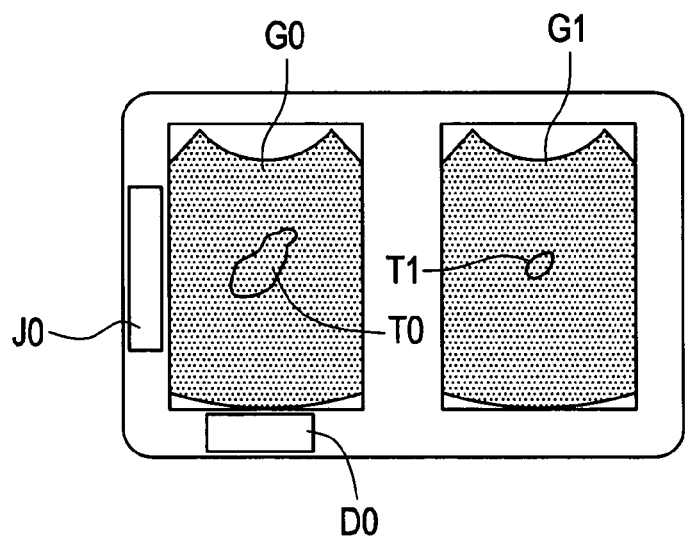
FIG. 5 is an explanatory diagram showing a screen on which the reference image and a real-time image are displayed side by side.

At Step R5, the ultrasonic diagnostic apparatus 100 produces an ultrasonic image, and as shown in FIG. 5, displays it as a real-time image G1 in the other section on the screen. T1 designates the region to be treated after medical treatment.

Figure 6:
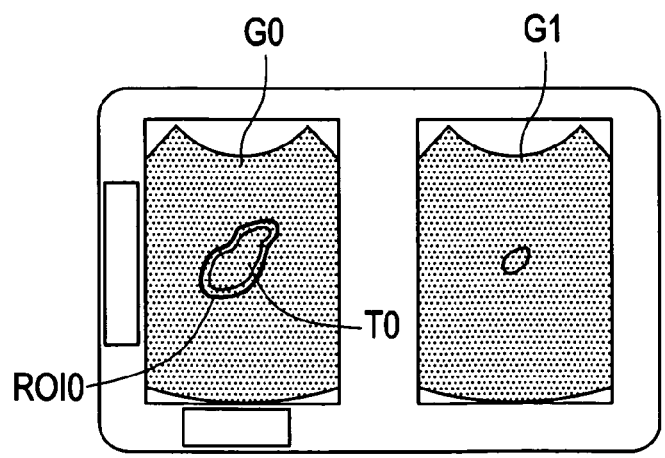
FIG. 6 is an explanatory diagram showing a screen on which a region of interest is specified in the reference image.

At Step R6, the operator specifies a region of interest ROI0 in the reference image G0 to encompass the region to be treated T0, as shown in FIG. 6.

Figure 7:
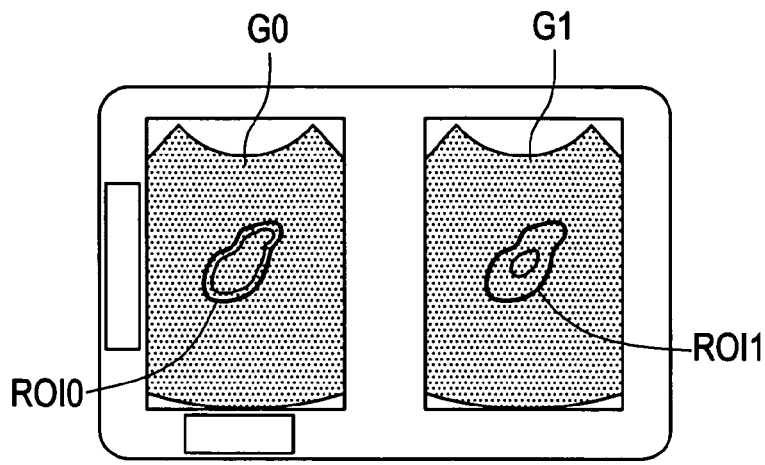
FIG. 7 is an explanatory diagram showing a screen on which a region of interest is automatically defined in the real-time image.

At Step R7, the ultrasonic diagnostic apparatus 100 automatically defines a region of interest ROI1 in the real-time image G1 corresponding to the region of interest ROI0 in the reference image G0, as shown in FIG. 7.

Figure 8:
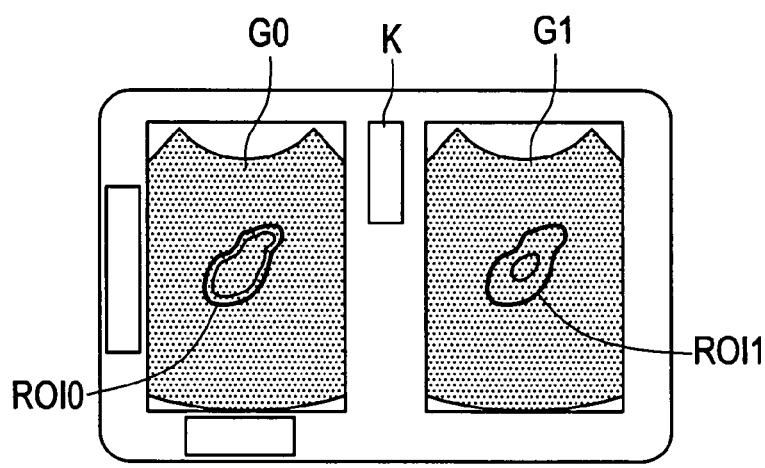
FIG. 8 is an explanatory diagram showing a screen on which a correlation coefficient is displayed.

At Step R8, the ultrasonic diagnostic apparatus 100 calculates a correlation coefficient between a portion outside of the region of interest ROI0 in the reference image G0 and a portion outside of the region of interest ROI1 in the real-time image G1, and displays the correlation coefficient K on the screen, as shown in FIG. 8.

Figure 9:
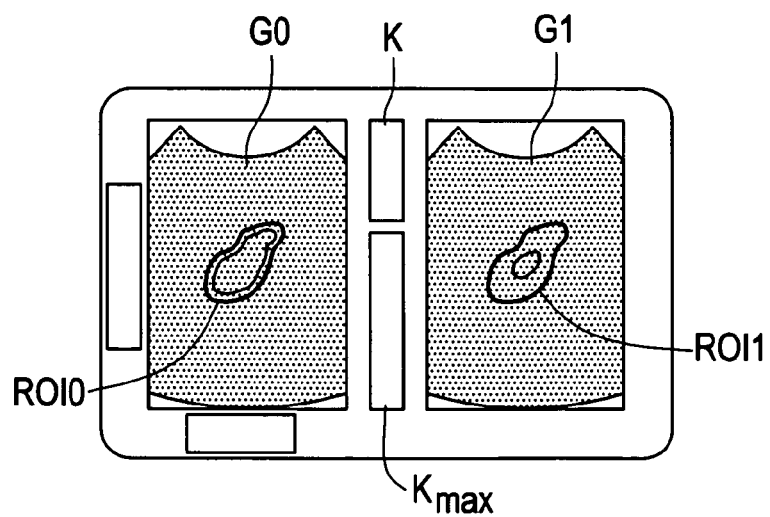
FIG. 9 is an explanatory diagram showing a screen on which the maximum correlation coefficient is displayed.

At Step R9, the ultrasonic diagnostic apparatus 100 updates a maximum correlation coefficient $K_{max}$ that holds the maximum value of the correlation coefficient from the beginning of acquisition of the real-time image up to the present, and displays the maximum correlation coefficient $K_{max}$ on the screen, as shown in FIG. 9.

At Step R10, the ultrasonic diagnostic apparatus 100 goes to Step R11 upon an operation for measurement by the operator; otherwise, to Step R12.

Figure 10:
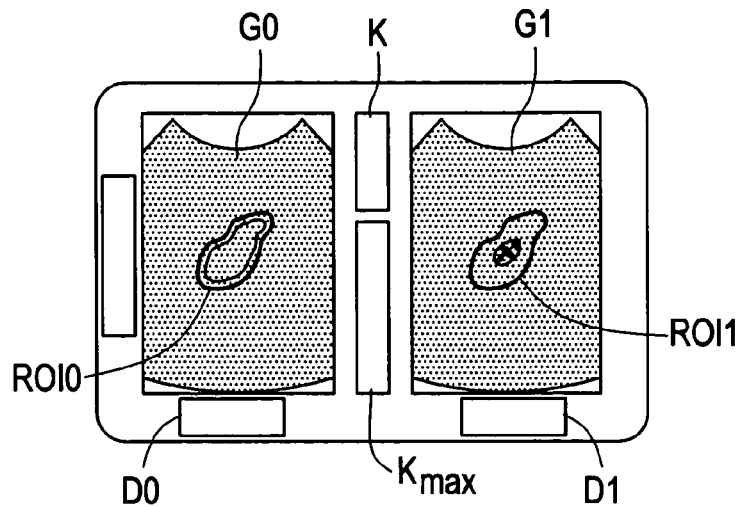
FIG. 10 is an explanatory diagram showing a screen on which a measurement result is displayed.

At Step R11, the ultrasonic diagnostic apparatus 100 measures the size or area of the portion specified by the operator, and displays a measurement result D1, as shown in FIG. 10. The flow then proceeds to Step R12.

At Step R12, the ultrasonic diagnostic apparatus 100 goes to Step R13 if the operator issues a command to superimpose the images; otherwise, to Step R14.

Figure 11:
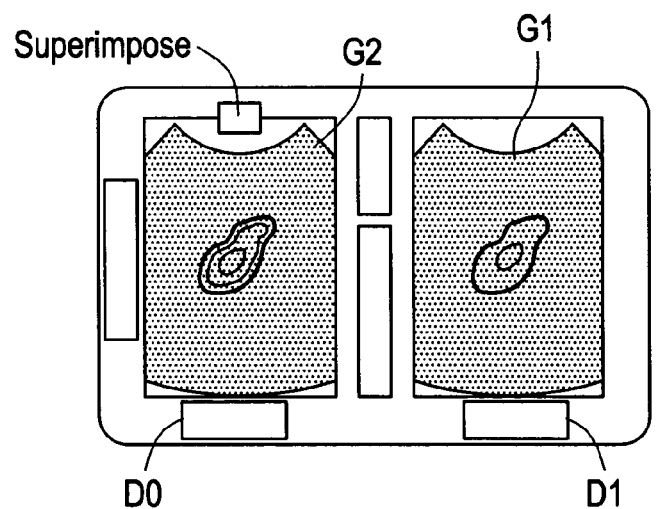
FIG. 11 is an explanatory diagram showing a screen on which the reference image and real-time image are displayed superimposed.

At Step R13, the ultrasonic diagnostic apparatus 100 displays a superimposed image G2 in which the reference image G0 is superimposed with the real-time image R1, as shown in FIG. 11. If the operator issues a command to release the superimposition, the display of superimposed image G2 is restored to the display of the reference image G0, and the flow proceeds to Step R14.

At Step R14, the ultrasonic diagnostic apparatus 100 terminates the processing if the operator issues a termination command; otherwise, goes to Step R15.

At Step R15, the operator performs a scan while adjusting the way in which the ultrasonic probe 1 is put against the subject so that the correlation coefficient K becomes equal to the maximum correlation coefficient $K_{max}$.

At Step R16, the ultrasonic diagnostic apparatus 100 produces an ultrasonic image and displays it as a real-time image G1 in the other section on the screen. The flow then goes back to Step R8.

In the ultrasonic diagnostic apparatus 100 in accordance with the first embodiment, since a real-time image is acquired with the same scan condition as that of a reference image, the reference image and real-time image can be suitably compared.

Figure 12:
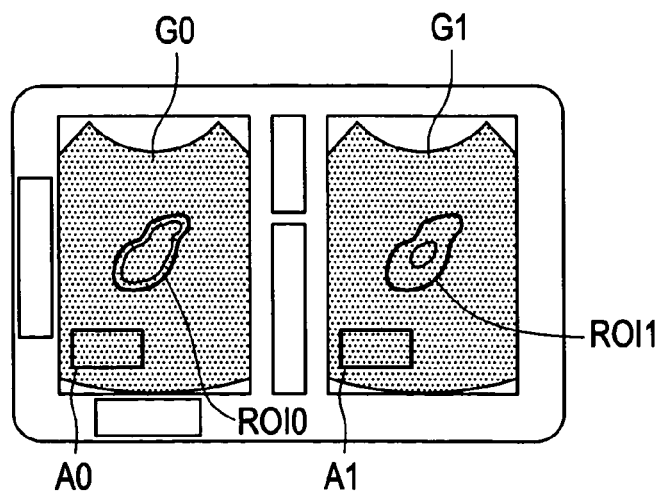
FIG. 12 is an explanatory diagram showing a screen on which a correlation comparison region is defined in the reference image.

Moreover, as shown in FIG. 12, correlation comparison regions A0 and A1 may be defined outside of the regions of interest ROI0 and ROI1 to calculate a correlation coefficient between the correlation comparison regions A0 and A1. By defining the correlation comparison region A0 and A1 to calculate a correlation coefficient, the processing load in the correlation calculation is reduced.

Second Embodiment

The configuration of the ultrasonic diagnostic apparatus in accordance with a second embodiment is similar to that of the ultrasonic diagnostic apparatus 100 in the first embodiment. However, a two-dimensional array ultrasonic probe 1' shown in FIG. 14 is used.

Figure 13:
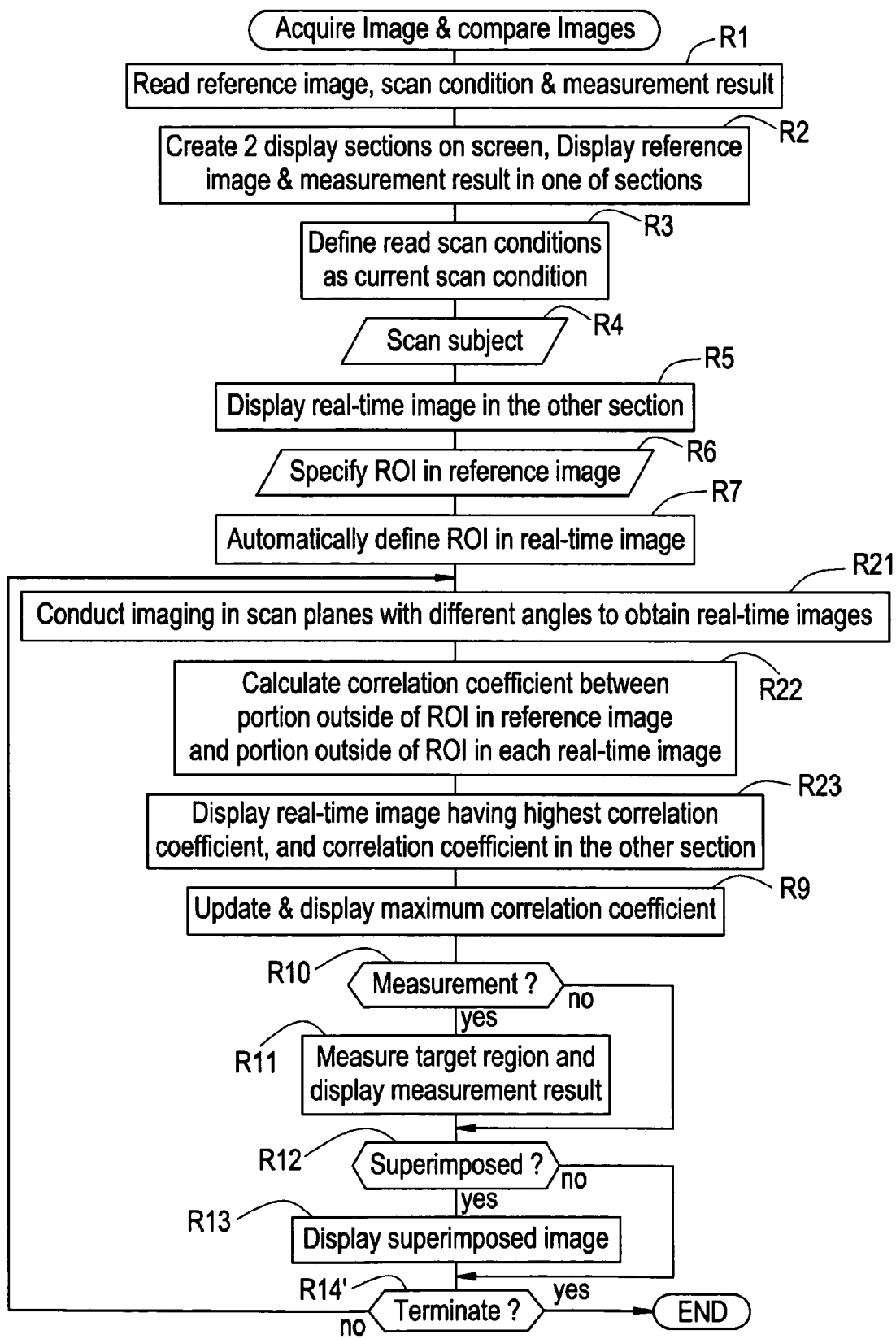
FIG. 13 is a flow chart showing operations and processes in acquiring a real-time image and comparing it with a reference image by the ultrasonic diagnostic apparatus in accordance with a second embodiment.

FIG. 13 is a flow chart showing operations and processes in acquiring a real-time image and comparing it with a reference image by the ultrasonic diagnostic apparatus in accordance with the second embodiment.

Step R1-Step R7 are the same as those shown in FIG. 3.

Figure 14:
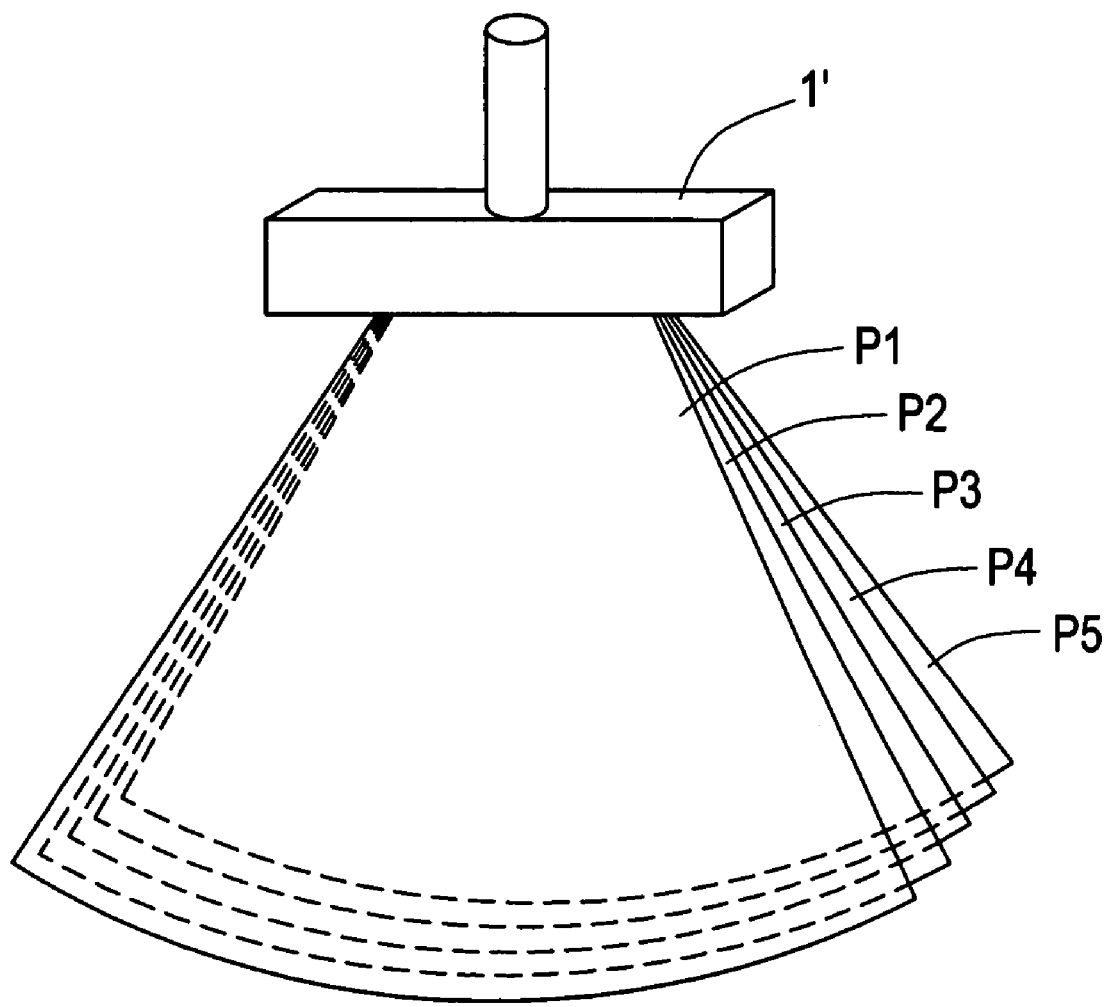
FIG. 14 is an explanatory diagram showing a plurality of scan planes with different angles.

At Step R21, the ultrasonic diagnostic apparatus 100 conducts imaging in a plurality of scan planes P1-P5 with different angles, as shown in FIG. 14, to produce a plurality of real-time images.

At Step R22, the ultrasonic diagnostic apparatus 100 calculates a correlation coefficient between a portion outside of the region of interest ROI0 in the reference image G0 and a portion outside of the region of interest in each of the real-time images.

At Step R23, the real-time image having the highest correlation coefficient is selected and displayed in the other section on the screen. Its correlation coefficient K is also displayed.

Step R9-Step R13 are the same as those shown in FIG. 3.

At Step R14', if the operator issues a termination command, the ultrasonic diagnostic apparatus 100 terminates the processing; otherwise, goes back to Step R21.

In the ultrasonic diagnostic apparatus in accordance with the second embodiment, since a plurality of real-time images are acquired at different scan plane angles, and the real-time image having the highest correlation coefficient with respect to the reference image is selected and displayed, it is permissible to put the ultrasonic probe 1' against a subject somewhat imprecisely, and, therefore, the work load on a human operator is reduced.

Instead of electronically changing the scan plane angle using the two-dimensional array ultrasonic probe 1', the angle of the regular ultrasonic probe 1 may be mechanically changed.

Other Embodiments

While comparison is made between an ultrasonic image before medical treatment as a reference image and a real-time image after medical treatment in the first and second embodiments, comparison may be made between an exemplary ultrasonic image acquired by a teacher or the maker of the ultrasonic diagnostic apparatus as a reference image and a real-time image acquired by a student or user. This makes it easier for the student or user to learn the skill of scanning.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic imaging method comprising the steps of:
   generating a reference image of a subject;
   storing the reference image and a scan condition used to acquire said reference image;
   reading said reference image and said scan condition, said reference image comprising a region of treatment encompassed by a region of interest before providing medical treatment to the subject;

setting the scan condition as a current scan condition before providing medical treatment;

acquiring a real-time image of the subject after providing medical treatment to the subject;

automatically defining the region of interest in said real-time image encompassing the region of treatment after providing medical treatment to the subject;

calculating a correlation coefficient between a portion outside of the region of interest in said reference image and a portion outside of the region of interest in the real-time image;

displaying on an ultrasonic image display device said reference image and said real-time image side by side, the correlation coefficient, and in a hold manner, a maximum value of the correlation coefficient from a beginning of acquisition of said real-time image up to the present; and adjusting an orientation of an ultrasonic probe against the subject so that the correlation coefficient becomes equal to the maximum value.

2. The ultrasonic imaging method of claim 1, further comprising a step of:

displaying said reference image and said real-time image superimposed in response to a command by an operator.

3. The ultrasonic imaging method of claim 1, further comprising the steps of:

storing a measurement result for a target region in said reference image; and reading said measurement result and displaying said measurement result when displaying said reference image.

4. The ultrasonic imaging method of claim 1, further comprising a step of:

storing said reference image and said scan condition in a server on a network.

5. An ultrasonic diagnostic apparatus comprising:

an ultrasonic probe;

a transmitting/receiving device for driving said ultrasonic probe to transmit ultrasonic pulses into a subject and receive ultrasonic echoes from inside the subject and outputting received data;

an ultrasonic image producing device for producing an ultrasonic reference image from the resulting received data, wherein said ultrasonic image producing device is configured to produce a real-time image, said real-time image acquired after providing medical treatment to the subject;

a reference image storage device for storing said reference image, said reference image comprising a region of interest encompassing a region of treatment before providing medical treatment to the subject;

a scan condition storage device for storing a scan condition for said reference image;

an automatic scan condition setting device for reading said scan condition and setting said scan condition as a current scan condition before providing medical treatment;

an automatic region defining device for defining in said real-time image the region of interest encompassing the region of treatment after providing medical treatment to the subject;

a correlation calculating device for calculating a correlation coefficient between a portion outside of the region of interest in said reference image and a portion outside of the region of interest in the real-time image;

an ultrasonic image display device for reading said reference image and displaying said reference image and said real-time image side by side; and a correlation coefficient display device for displaying the correlation coefficient, and in a hold manner, a maximum value of the correlation coefficient from the beginning of acquisition of said real-time image up to the present;

wherein said ultrasonic probe is configured to be adjusted against the subject so that the correlation coefficient becomes equal to the maximum correlation coefficient.

6. The ultrasonic diagnostic apparatus of claim 5, further comprising:

a combined-display device for displaying said reference image and said real-time image superimposed in response to a command by an operator.

7. The ultrasonic diagnostic apparatus of claim 5, further comprising:

a measurement result storage device for storing a measurement result for a target region in said reference image; and a measurement result display device for reading said measurement result and displaying said measurement result when displaying said reference image.

8. The ultrasonic diagnostic apparatus of claim 5, wherein said reference image storage device and said scan condition storage device reside in said ultrasonic diagnostic apparatus, and in a server on a network.

9. The ultrasonic diagnostic apparatus of claim 5, wherein said reference image storage device and said scan condition storage device reside not in said ultrasonic diagnostic apparatus but in a server on a network.

10. An ultrasonic diagnostic apparatus comprising:

an ultrasonic probe;

a transmitting/receiving device for driving said ultrasonic probe to transmit ultrasonic pulses into a subject and receive ultrasonic echoes from inside the subject and outputting received data;

an ultrasonic image producing device for producing an ultrasonic reference image from the resulting received data;

a reference image storage device for storing said reference image, said reference image comprising a region of treatment encompassed by a region of interest before providing medical treatment to the subject;

a scan condition storage device for storing a scan condition for said reference image;

an automatic scan condition setting device for reading said scan condition and setting said scan condition as a current scan condition before providing medical treatment;

a scan plane angular scanning device for acquiring a plurality of real-time images at different scan plane angles, said plurality of real-time images acquired after providing medical treatment;

an automatic region defining device for defining in said plurality of real-time images the region of treatment encompassed by the region of interest after providing medical treatment to the subject;

a correlation coefficient calculating device for calculating a correlation coefficient between a portion outside of the region of interest in said reference image and a portion outside of the region of interest in each of said real-time images;

an ultrasonic image display device for displaying said reference image and one of said real-time images having a highest correlation coefficient side by side, and a correlation coefficient display device for displaying said highest correlation coefficient.

* * * * *